United States Patent
Hardy

(12) 
(10) Patent No.: US 10,585,333 B1
(45) Date of Patent: Mar. 10, 2020

(54) SEALED DOME LIGHT FOR INSPECTION SYSTEMS

(71) Applicant: Spectrum Illumination Co., Montague, MI (US)

(72) Inventor: David J. Hardy, Howard City, MI (US)

(73) Assignee: Spectrum Illumination Co., Montague, MI (US)

( * ) Notice: Subject to any disclaimer, the term of this patent is extended or adjusted under 35 U.S.C. 154(b) by 0 days.

(21) Appl. No.: 16/152,610

(22) Filed: Oct. 5, 2018

(51) Int. Cl.
| | |
|---|---|
| *G03B 15/03* | (2006.01) |
| *F21V 3/02* | (2006.01) |
| *F21V 31/00* | (2006.01) |
| *F21V 3/04* | (2018.01) |
| *F21V 23/00* | (2015.01) |
| *F21L 4/00* | (2006.01) |
| *G06T 7/00* | (2017.01) |
| *F21Y 105/18* | (2016.01) |

(52) U.S. Cl.
CPC .............. *G03B 15/03* (2013.01); *F21V 3/02* (2013.01); *F21V 3/049* (2013.01); *F21V 23/001* (2013.01); *F21V 31/005* (2013.01); *F21Y 2105/18* (2016.08); *G06T 7/0004* (2013.01)

(58) Field of Classification Search
CPC .......... F21V 31/03; F21V 7/008; F21V 7/045; F21Y 2105/18
USPC ......................................... 362/16, 158, 350
See application file for complete search history.

(56) References Cited

U.S. PATENT DOCUMENTS

| | | | | |
|---|---|---|---|---|
| 8,172,434 | B1* | 5/2012 | Olsson ..................... | B63B 45/00 362/346 |
| 9,784,417 | B1* | 10/2017 | Springer .................. | F21K 9/238 |
| 2010/0246195 | A1* | 9/2010 | Muller ...................... | F21S 8/00 362/375 |
| 2018/0352121 | A1* | 12/2018 | Chapman ............. | H04N 5/2252 |

OTHER PUBLICATIONS

Spectrum Illumination MDL 7.25 Mount Drawing, which was on sale in the United States since prior to 2015.
Spectrum Illumination MDL 7.25 Dome Light Monster Light, which was on sale in the United States since prior to 2015.
Spectrum Illumination MDL 7.25 Dome Light patent drawing, which was on sale in the United States since prior to 2015.

* cited by examiner

*Primary Examiner* — Evan P Dzierzynski
*Assistant Examiner* — Keith G. Delahoussaye
(74) *Attorney, Agent, or Firm* — Warner Norcross + Judd LLP

(57) ABSTRACT

A sealed dome light assembly for an inspection system includes a substantially dome-shaped upper housing, an annular lower housing, a plurality of light sources, and an annular cover. The upper housing includes an annular lower flange and an aperture through an apex of the upper housing. The lower housing includes a plurality of spaced light seats disposed within the lower housing. Each of the plurality of light sources is mounted within a respective one of the plurality of light seats and recessed below an upper surface of the lower housing. The cover covers the lower housing, and the cover and the lower housing define a sealed interface therebetween to provide a water-tight sealed enclosure to protect the light sources disposed within the lower housing.

9 Claims, 5 Drawing Sheets

SEALED DOME LIGHT FOR INSPECTION SYSTEMS

BACKGROUND OF THE INVENTION

The present invention relates to illumination for an inspection system, and more particularly to a sealed dome light for a machine vision inspection system.

Camera based inspection systems are commonly used in industrial settings to automate the inspection of products. Camera based inspection systems, commonly referred to as "machine vision" systems, can identify defects or contamination at a fast rate and for very small parts. High intensity LEDs provide proper illumination for high-speed camera equipment to take pictures of products being manufactured or assembled, often as the product passes by one or more particular points on an assembly line. The pictures are analyzed by a computer to determine if there are any defects in the product.

In order for the computer to analyze the photographs, it is desirable that the illumination of the product be nearly uniform for all of the pictures taken by the camera. This uniformity in lighting helps prevent the computer from misinterpreting the photographs due to changed lighting conditions. Illumination can be provided in various forms including direct illumination, ring illumination, horizontal illumination, coaxial illumination, and dome illumination. Dome illumination, in particular, works very well for inspecting irregularly shaped objects. Dome lights are used to create even lighting on shiny or uneven surfaces.

Dome illuminators or lights generally include a hemispherical dome that overlies an object to be inspected. A light source, such as a ring of LEDs, is located within the dome. The dome light includes a central opening that provides a viewing window for an associated camera. The camera takes pictures of the products positioned below the dome light. Dome lights used in industrial settings, including for the production of consumables, can get dirty, dusty, and/or contaminated and require cleaning to continue providing proper illumination. One issue with cleaning dome lights is that the LEDs, though seated within their ring, are not protected and may be exposed to water or other cleaning fluids. Thus, it would be desirable to provide a dome light that is sealed to protect the LEDs and other interior components, making the dome light readily cleanable.

SUMMARY OF THE INVENTION

The noted problems are addressed by the present invention. According to various embodiments, a sealed dome light assembly for an inspection system includes a substantially dome-shaped upper housing, an annular lower housing, a plurality of light sources, and an annular cover. The upper housing includes an annular lower flange and an aperture in an apex of the hemispherical upper housing. The lower housing includes a plurality of spaced light seats disposed within the lower housing. Each of the plurality of light sources is mounted within a respective one of the plurality of light seats. The cover covers the lower housing and is disposed between the lower housing and the upper housing. The cover and the lower housing define a sealed interface therebetween and provide a water-tight sealed enclosure to protect the light sources disposed within the lower housing.

According to one embodiment of the present invention, the lower housing of the dome light includes upper and lower surfaces, each including circumferentially spaced inner and outer grooves. The dome light assembly includes inner O-rings and outer O-rings seated within each of the respective inner and outer grooves to provide upper and lower sealed interfaces between the cover, lower housing, and a base plate, respectively. Thus, the lower housing is sealed and provides a sealed enclosure for the components located within the lower housing.

According to other aspect of the present disclosure, the dome light includes an annular base plate to which the lower housing is mounted. The lower surface of the lower housing can include at least one annular wiring channel, and the lower sealed interface between the base plate and the lower housing provides a water-tight enclosure for wiring disposed within the wiring channels. As such, the plurality of light sources and wiring are protected from exposure to contaminants and fluid during normal use and cleaning of the dome light.

In at least one embodiment, the dome light includes a plurality of spacers disposed between the dome housing's lower flange and the cover. The spacers are configured to provide a gap between the dome housing and the cover for fluid to drain therefrom, so that fluid is not entrapped within the dome light during/after cleaning the dome light.

According to another embodiment, the plurality of light sources are arranged such that light passes through the cover, reflects off the interior of the dome housing, and is directed toward an open bottom of the dome light assembly to illuminate a target object located below. Light, reflected off the interior of the hemispherical housing, follows many different pathways, which eliminates substantially all shadows on the target object positioned below the dome light assembly. Light also passes through the cover, which can be can be substantially translucent or can be opaque and may serve as a light diffuser.

According to one aspect of the present disclosure, the dome light assembly provides a sealed housing for protecting the components, primarily as housed within the lower housing, from exposure to water and/or cleaning products or fluids used in cleaning the equipment, as well as any contaminants introduced during normal use of an associated inspection system. Lights and wiring enclosed within the lower housing, which could be damaged by exposure to contaminants, water, or other fluids utilized during cleaning, are protected by the sealed lower housing, making the dome light assembly readily cleanable. Further, the gap between the upper housing and the cover provides a path for fluid drainage such that fluids are not entrapped within the dome light assembly during/after cleaning.

These and other features and advantages of the invention will be more fully understood and appreciated by reference to the entire application including the specification, the claims, and the drawings.

DESCRIPTION OF THE CURRENT EMBODIMENTS

Figure 1:
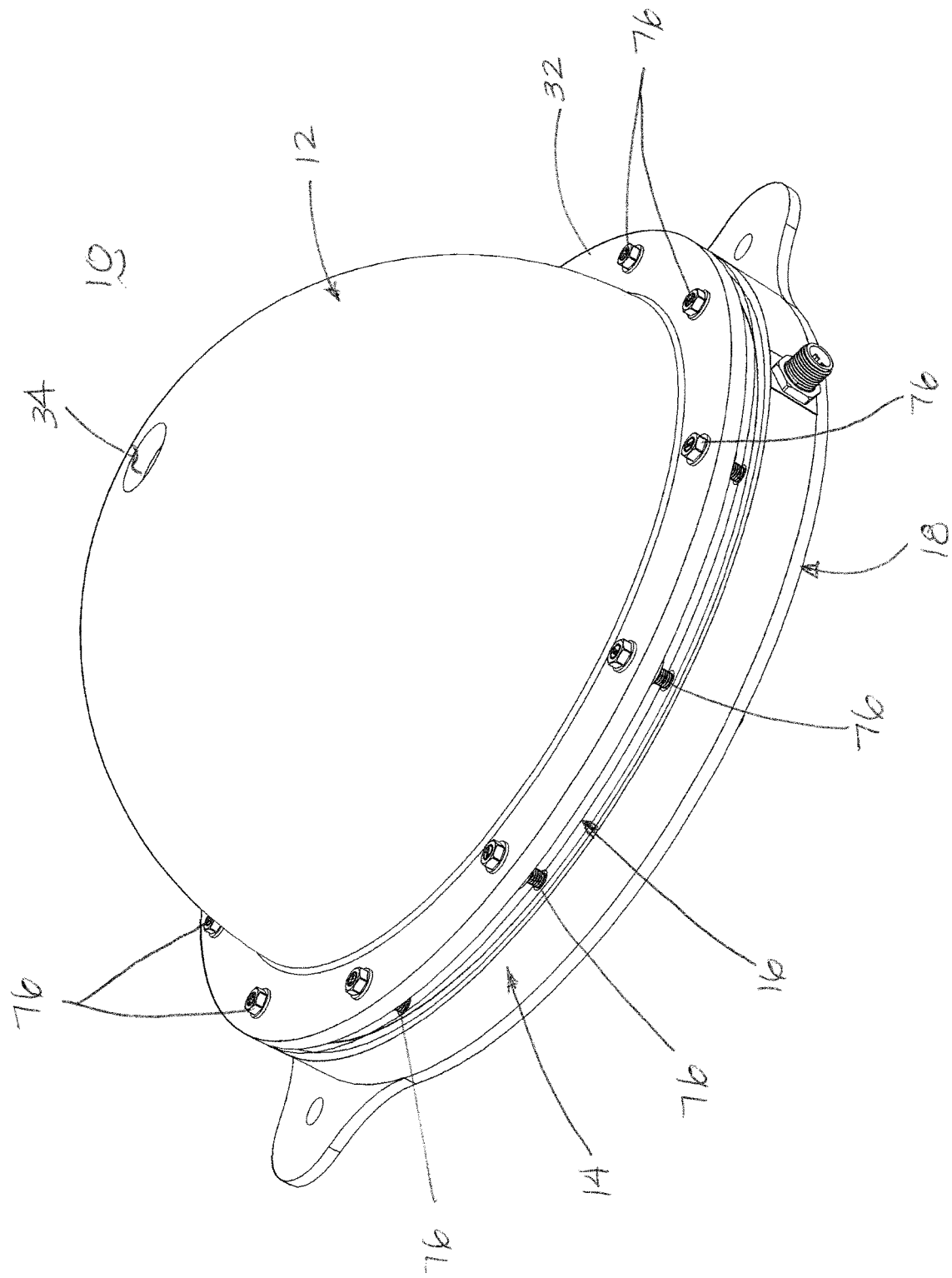
FIG. 1 is a perspective view of a dome light assembly according to one embodiment of the disclosure.
Figure 2:
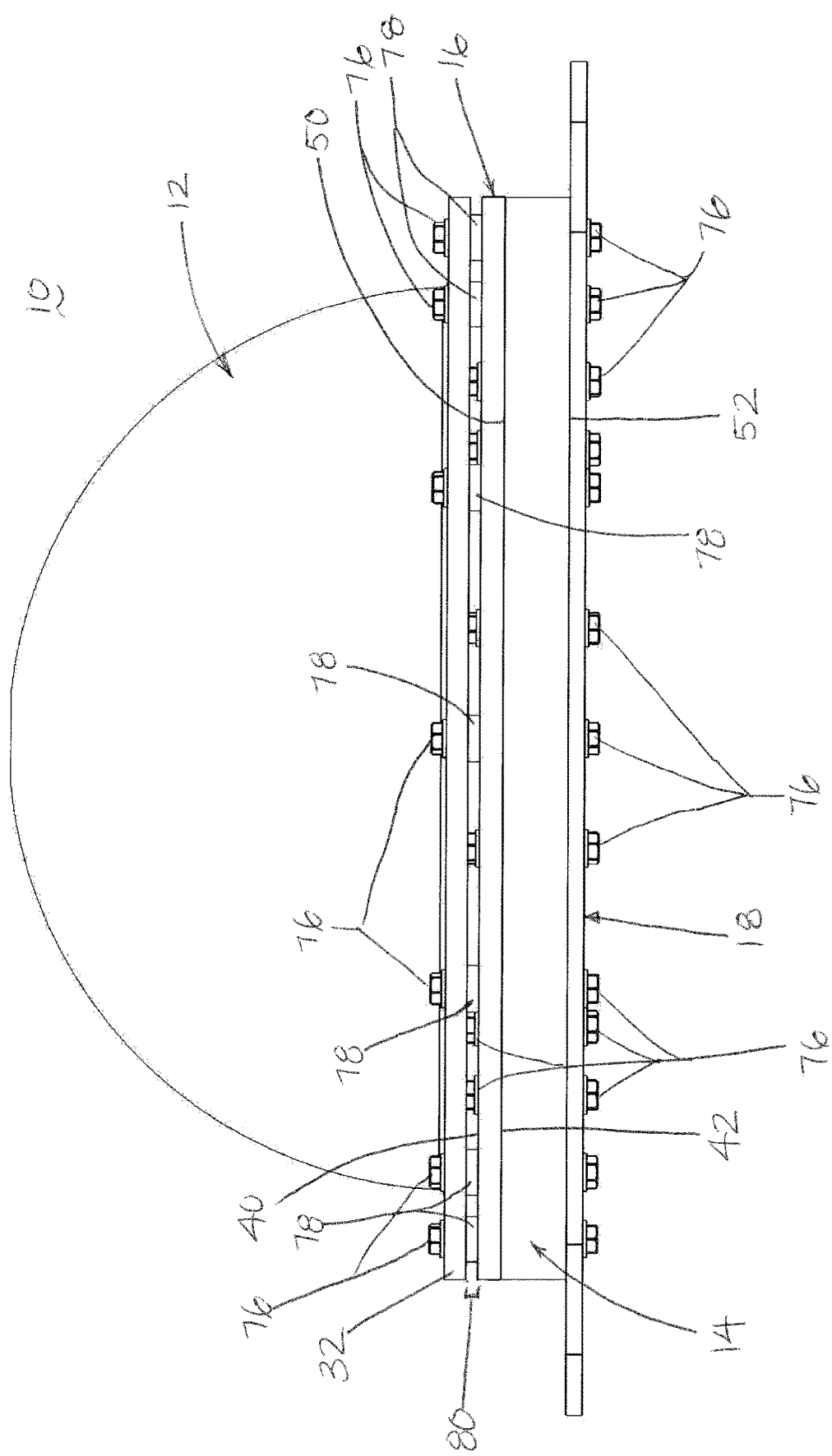
FIG. 2 is a side view of the dome light assembly of FIG. 1.
Figure 3:
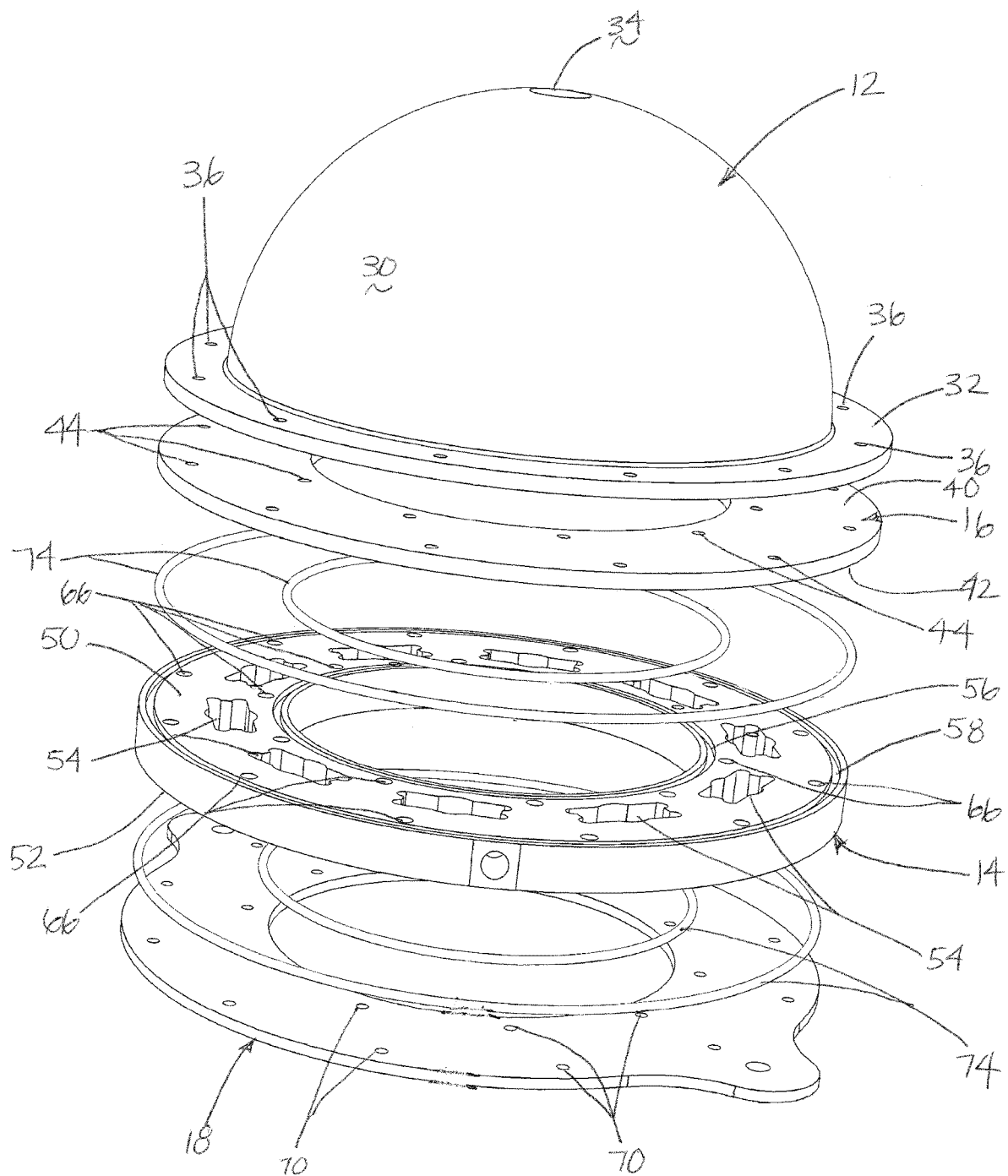
FIG. 3 is an exploded perspective view of a portion of the dome light assembly of FIG. 1, with fasteners and spacers removed.

A sealed dome light assembly in accordance with one embodiment is illustrated in FIGS. 1-5. The dome light 10 is particularly adapted for use with camera based inspection systems, commonly referred to as "machine vision" systems. Machine vision inspection systems are camera-based inspection systems that can identify nonconformities, such as manufacturing errors or contamination, at a faster rate, more reliably, and/or for smaller parts than is humanly possible. Such systems generally include a high speed, high resolution camera for capturing high resolution images of the object to be inspected, referred to herein as the target object. The images are analyzed by an associated computer to determine if there are any defects or nonconformities present in the target object. Machine vision systems also typically include a light source to properly illuminate the target object, which is typically located below the light source and camera.

One type of illumination used in machine vision inspection systems is diffuse illumination. Diffuse illumination is supplied by a light source positioned within a substantially hemispherical housing such that light is generated from many directions or angles. The light reflects off the interior of the hemispherical housing and follows many different pathways, which eliminates substantially all shadows on the target object.

Referring to FIGS. 1-5, the dome light 10 includes a dome-shaped upper housing 12, a lower housing 14, a cover 16, and a base plate 18. The dome housing 12 is a hollow, substantially hemispherical housing with an open bottom and a reflective interior surface 30. The dome housing 12 includes an annular lower flange 32 and an aperture 34 through the apex of the dome housing 12. Multiple, radially spaced fastener holes 36 (see FIG. 3) are disposed around the flange 32. The dome housing 12 can be formed of a white diffuse plastic material, or any other suitable material.

The cover or diffuser 16 is a substantially clear or translucent annular member that defines an upper surface 40 and a lower surface 42. Multiple, radially spaced fastener holes 44 (see FIG. 3) are disposed through the cover 16. The cover 16 is positioned between the dome housing 12 and the lower housing 14.

The lower housing 14 is an annular member that defines an upper surface 50 and a lower surface 52. The lower housing 14 is made from at least a partially translucent material, in some embodiments. The lower housing 14 includes a plurality of light seats 54 and fastener holes 66 (see FIG. 3) that are radially spaced about the housing 14. The light seats 54 are recessed into the lower housing 14, below the upper surface 50. The upper surface 50 and the lower surface 52 include circumferentially spaced inner grooves 56, 60 and an outer grooves 58, 62, respectively. The lower surface 52 also includes at least one annular wiring channel 64 (see FIG. 4). The cover 16 covers the upper surface 50 of the lower housing 14.

The dome assembly 10 can also include the annular base plate 18. The base plate 18 is a flat member that can include ears, tabs, etc. for mounting the dome assembly 10 to a structural member of the inspection system. The base plate 18 also includes a plurality of radially spaced fastener holes 70 (see FIG. 3). The base plate 18 is mounted to the lower surface 52 of the lower housing 14.

The dome assembly 10 includes a plurality of light sources (not shown), for example LEDs, mounted within the light seats 54 in the lower housing 14. The lights are electrically connected with wiring (not shown) routed through the lower housing wiring channels 64. The lights are recessed below the upper surface 50 of the lower housing 14 and are enclosed within the light seats 54 by the cover 16.

Figure 4:
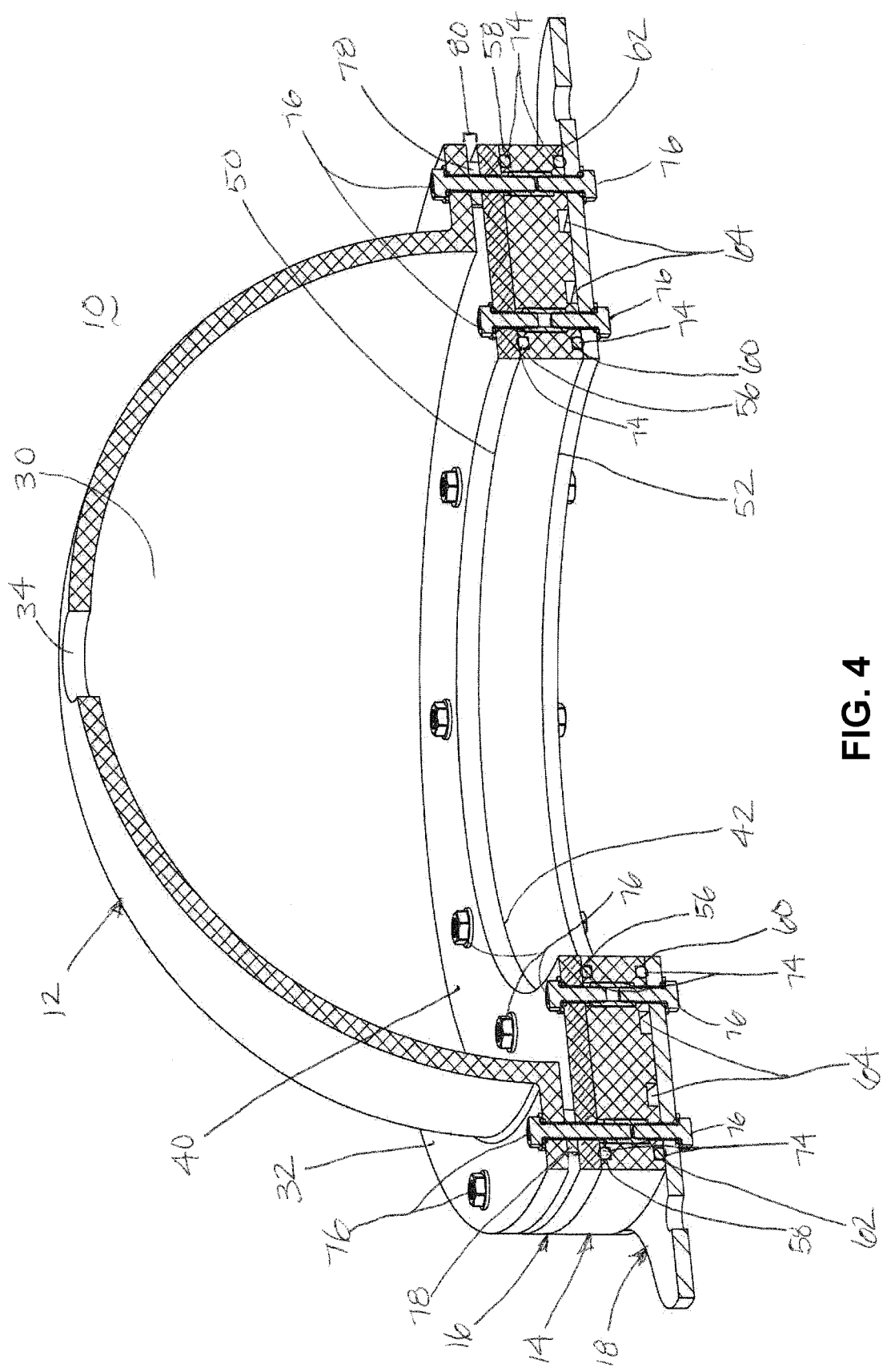
FIG. 4 is a cross section of the dome light assembly, taken through a spacer of the dome light assembly.
Figure 5:
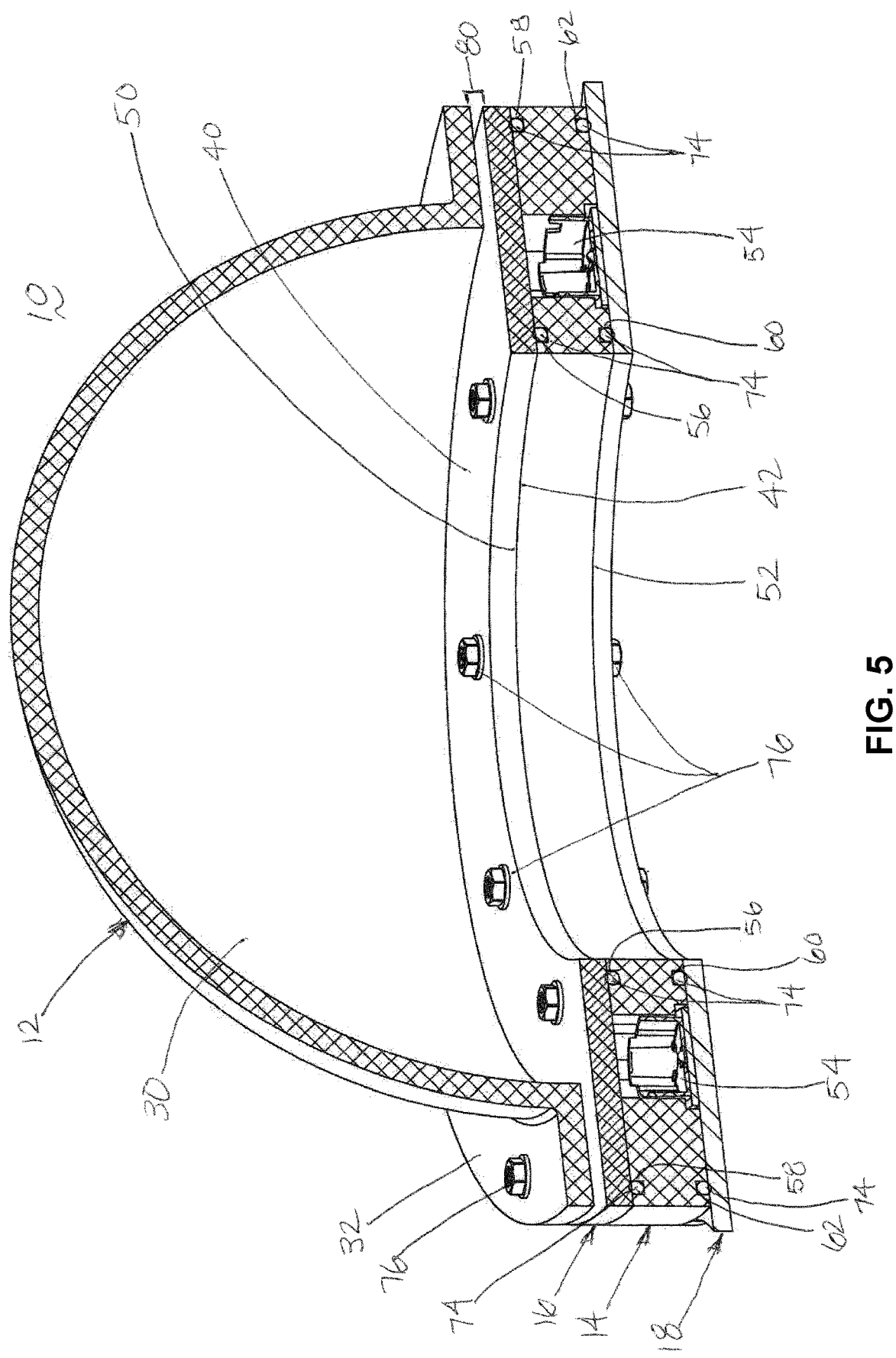
FIG. 5 is a cross section of the dome light assembly, taken through a light seat of the dome light assembly.

The dome assembly 10 includes at least two O-rings 74. More specifically, 0-rings 74 are seated within each of the grooves 56-62 in the upper surface 50 and lower surface 52 of the lower housing 14, as shown in FIGS. 4 and 5. The O-rings 74 are made of a flexible, compressible material that, when sandwiched between the cover 16 and lower housing 14, or between the lower housing 14 and base plate 18, seal the interfaces between the cover 16 and the lower housing 14 and between the lower housing 14 and the base plate 18, respectively. The upper sealed interface provides a water-tight enclosure for the lights disposed within the light seats 54 of the lower housing 14. The lower sealed interface provides a water-tight enclosure for the wiring that is routed through the lower housing wiring channels 64. Further, the base plate 18, lower housing 14, cover 16, and dome housing 12 are affixed to their adjacent component(s) with a plurality of sealing fasteners 76. The fasteners can include O-rings or sealing washers to provide water-tight adjoining of components. Thus, the lower housing 14 is completely sealed and provides a sealed enclosure for the components located within the housing 14.

The dome assembly 10 also includes a plurality of spacers 78 disposed between the dome housing lower flange 32 and the cover 16. The spacers 78 provide a gap 80 between the sealed lower housing 14 and the dome housing 14, the purpose of which will be discussed hereinafter.

In use, light from the multiple lights passes through the cover 16, reflects off the interior 30 of the dome housing 12, and is directed toward the open bottom of the dome light 10. The reflected light follows many different pathways, which eliminates substantially all shadows on the target object positioned below the dome light 10.

In conjunction with a machine vision inspection system, a camera (not shown) can be disposed above the aperture 34 in the dome housing 12 to view and capture an image of a target object (not shown) located below the dome light 10. As described above, the target object receives a uniform distribution of light coming from the entire concave interior surface 30 of the dome housing 12.

Machine vision inspection systems are generally used in industrial manufacturing settings, food-grade manufacturing, and food packaging and can become dirty and/or contaminated. Good sanitization practices require cleaning of the inspection system components, including the dome light 10. The present dome light 10 provides a sealed housing for protecting the components, primarily as housed within the lower housing 14, from exposure to water used for cleaning and/or any cleaning products or fluids used in the cleaning of the equipment, as well as any contaminants introduced during normal use of the inspection system. More specifically, the lights and wiring enclosed within the lower housing 14, which could be damaged by exposure to contaminants, water, or other fluids utilized during cleaning, are protected by the sealed lower housing 14, making the dome light 10 readily cleanable. Further, the gap 80 between the dome housing 12 and the cover 16 provides a path for fluid drainage such that fluids are not entrapped within the dome light 10 during/after cleaning.

The above descriptions are those of current embodiments of the invention. Various alterations and changes can be made without departing from the spirit and broader aspects of the invention as defined in the appended claims, which are to be interpreted in accordance with the principles of patent law including the doctrine of equivalents. Any reference to elements in the singular, for example, using the articles "a," "an," "the," or "said," is not to be construed as limiting the element to the singular.

The invention claimed is:

1. A sealed dome light assembly for an inspection system, the dome light assembly comprising:
    a substantially dome-shaped upper housing including an annular lower flange and at least one aperture in the upper housing;
    an annular lower housing including a plurality of spaced light seats disposed within the lower housing, the lower housing including an upper surface in which is defined a first inner groove and a first outer groove and a lower surface in which is defined a second inner groove and a second outer groove, wherein the lower surface further includes an annular wiring channel;
    a first inner O-ring and a first outer O-ring seated within the first inner and first outer grooves, respectively;
    a plurality of light sources each being mounted within a respective one of the plurality of light seats such that light from the plurality of light sources reflects off an interior of the dome-shaped upper housing and is directed toward an open bottom of the dome light assembly;
    a clear annular cover covering the lower housing and being disposed between the lower housing and the upper housing;
    a plurality of spacers disposed between the upper housing's lower flange and the annular cover, wherein the spacers are configured to provide liquid drainage between the upper housing and the annular cover;
    an annular base plate to which the lower housing is mounted;
    a second inner O-ring and a second outer O-ring seated within the second inner and second outer grooves, respectively;
    wherein the annular cover, the first inner O-ring, the first outer O-ring, and the lower housing define a first sealed interface between the annular cover and the lower housing; and
    wherein the base plate, second inner O-ring, second outer O-ring, and lower housing define a second sealed interface between the lower housing and the base plate, wherein the first and second sealed interfaces provide a water-tight sealed enclosure for the light sources.

2. The sealed dome light assembly of claim 1, wherein the base plate, lower housing, cover, and upper housing's lower flange include a plurality of spaced holes, and a plurality of sealing fasteners affix respective ones of the base plate, lower housing, cover, and upper housing's lower flange together.

3. A sealed dome light assembly for use with a machine vision inspection system, the dome light assembly comprising:

a dome housing including an annular lower flange, at least one aperture in the dome housing, and a reflective interior surface;
    an annular lower housing defining an upper surface and a lower surface and including a plurality of spaced light seats recessed below the upper surface, the upper surface including circumferentially spaced grooves;
    an annular diffuser covering the upper surface of the lower housing;
    a plurality of spacers disposed between the dome housing's lower flange and the diffuser to provide a gap between the dome housing and the diffuser such that fluid may drain between the dome housing and the diffuser;
    a plurality of light sources each mounted within a respective one of the plurality of light seats, the plurality of light sources arranged such that light passes through the diffuser, reflects off the interior of the dome housing, and is directed toward an open bottom of the dome light assembly; and
    at least two O-rings, the O-rings disposed in the circumferentially spaced grooves in the upper surface of the lower housing, the O-rings providing a sealed interface between the diffuser and the lower housing, thereby providing a water-tight enclosure for the light sources disposed within the light seats of the lower housing.

4. The sealed dome light assembly of claim 3 further including an annular base plate mounted to the lower surface of the lower housing.

5. The sealed dome light assembly of claim 4, wherein the lower surface of the lower housing includes annular wiring channels.

6. The sealed dome light assembly of claim 5, wherein the lower surface of the lower housing includes circumferentially spaced grooves, and O-rings are disposed in the circumferentially spaced grooves in the lower surface of the lower housing, thereby providing a lower sealed interface between the base plate and the lower housing.

7. The sealed dome light assembly of claim 6, wherein lower sealed interface between the base plate and the lower housing provides a water-tight enclosure for wiring disposed within the wiring channels.

8. The sealed dome light assembly of claim 7 further including a plurality of sealing fasteners configured to sealingly affix respective ones of the base plate, lower housing, diffuser, and dome housing to one another.

9. The sealed dome light assembly of claim 8, wherein the at least one aperture provides a view through the open bottom of the dome light assembly to a target object located therebelow and upon which light from the light sources is directed,
    wherein one or more cameras disposed above the at least one aperture can capture an image of the target object.

* * * * *